United States Patent [19]

D'Haenens et al.

[11] 4,175,551
[45] Nov. 27, 1979

[54] ELECTRICAL MASSAGE DEVICE

[75] Inventors: Irnee J. D'Haenens, Thousand Oaks; Charles P. Ledergerber, Beverly Hills, both of Calif.

[73] Assignee: Electromed Incorporated, Beverly Hills, Calif.

[21] Appl. No.: 850,745

[22] Filed: Nov. 11, 1977

[51] Int. Cl.² ............................................. A61H 29/00
[52] U.S. Cl. ................................................. 128/24.4
[58] Field of Search .................... 128/24.4, 24.5, 418, 128/387, 389, 24.1

[56] References Cited

U.S. PATENT DOCUMENTS

| | | | |
|---|---|---|---|
| 602,950 | 4/1898 | Lau | 128/24.4 |
| 798,457 | 8/1905 | Schmidt | 128/24.4 |
| 872,126 | 11/1907 | Hart | 128/24.5 |
| 3,490,442 | 1/1970 | Streu | 128/418 |

FOREIGN PATENT DOCUMENTS 1480327  4/1967  France ................................. 128/24.4

*Primary Examiner*—Lawrence W. Trapp
*Attorney, Agent, or Firm*—Jessup & Beecher

[57] ABSTRACT

A massage device which utilizes the combination of electroneurological stimulation and mechanical massage for medical treatment of pain. The apparatus includes a housing having a massage head formed from a plurality of elongate rollers, connected to the electrical output of a pulse-generating circuit. The rollers form a mechanical massaging head, while the electrical pulses stimulate underlying nerves to block or reduce pain. A second or ground electrode is provided by an expansion band which can be easily slipped on an ankle or wrist and is connected to the main electrical circuit by a flexible electrical cord. The pulse-generating circuit includes a pair of switches for selecting a discrete voltage amplitude over a varying predetermined range, and a light-emitting diode to indicate operation of the pulse-generating circuit. Also included in the case or housing is a ball electrode for massaging and treating particular body points known as acupuncture or trigger points. The ball electrode is in the form of a roller ball installed in a ball socket in the housing, and is also connected to the output of the pulse-generating circuit.

8 Claims, 4 Drawing Figures

ELECTRICAL MASSAGE DEVICE

BACKGROUND OF THE INVENTION

This invention relates generally to massage devices and more particularly relates to electroneurological stimulating devices for treating and relieving pain.

The use of electricity to stimulate the nervous system for the treatment of pain has been long known in the art. The treatment is effected by providing for electrical stimulation of nerve fibers through the skin (transcutaneous) and has become a widely accepted method of providing pain relief. In the prior art devices a circuit sends electrical signals through the surface of the skin. One such device has a pair of rollers which serve respectively as work and ground electrodes for conducting small electrical pulses through the skin. Treatment with this type of device results in barely subdermal electrical current being conducted between adjacent rollers, with little or no resultant electrical stimulation of nerve fibers. Subsequent devices developed include a roller electrode with the ground electrode being formed by the handle of the device or by adhesive electrodes. These devices do not provide any method of treating a particular point, such as acupuncture points. The electrical circuits used in these previous devices generate dangerously high electrical output voltage, and could cause excessive stimulation, if not carefully used.

SUMMARY OF THE INVENTION

The purpose of the present invention is to provide a small, compact, electrical stimulator and mechanical massage device which provides effective treatment for pain and can be used for treatment of particular neurological points of the body.

The present invention provides an electrical neurological stimulator and mechanical massage device which is very compact in size and utilizes multiple elongate electrode rollers in conjunction with a ball electrode and an expansion wrist band indifferent (ground) electrode which makes the device convenient and easy to use. In addition, the device provides a multiple switch system permitting selection of pulse amplitudes in discretely variable steps.

The device has a case having a plurality of elongate rollers mounted adjacent to each other to form a curved roller head which is connected to a pulse-generating system through a transformer and switch system. In addition to the roller electrodes, a ball electrode is provided on the side of the case for treatment of particular selected trigger or acupuncture points on the body. Thus, the ball electrode serves as a point electrode which can be rolled over the point to be treated.

Use of the device is greatly simplified by an expansion band indifferent or ground electrode which can be easily slipped on the wrist or ankle and is connected to the main housing by a flexible cord. A light-emitting diode is coupled into the pulse-generating circuit to indicate proper operation. The switching system provides high or low-level current positions with a second switch permitting selection of four amplitude positions in either the high or low current modes. The pulse-generating electrical system is powered by a nine-volt battery.

It is one object of the present invention to provide an electrical stimulator and massage device which is convenient and easy to use.

Another object of the present invention is to provide an electrical stimulator and massage device which includes a ball electrode for stimulation of particular acupuncture points on the body to treat and relieve pain.

Yet another object of the present invention is to provide an electrical stimulator and massage device which utilizes an expansion band indifferent electrode for convenient operation.

Still another object of the present invention is to provide an electrical stimulator and massage device which permits selecting a variety of discrete current amplitudes.

Another object of the present invention is to provide an electrical stimulator and massage device which has high and low-level current positions with up to four variations of each of the high and low current positions.

Other objects, advantages and novel features of the invention will become apparent from the following detailed description of the invention when considered in conjunction with the accompanying drawings wherein like reference numbers identify like parts throughout.

DETAILED DESCRIPTION OF THE PREFERRED EMBODIMENT

Figure 1:
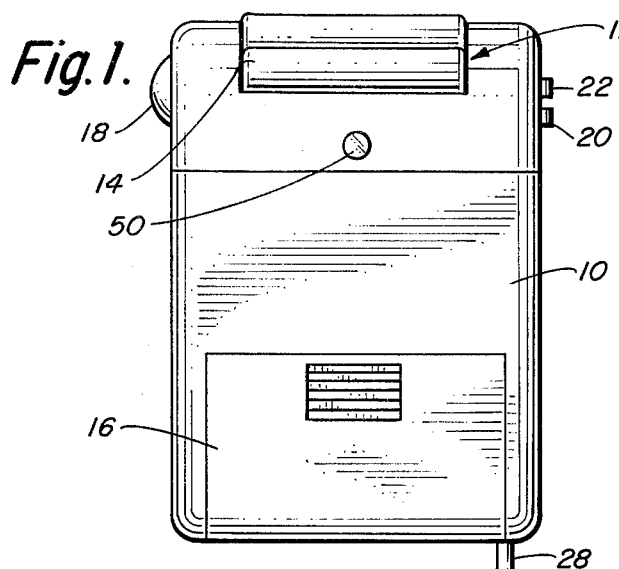
FIG. 1 is a front elevation of the electrical stimulation and massage device with the expansion band indifferent electrode connected to the device.
Figure 2:
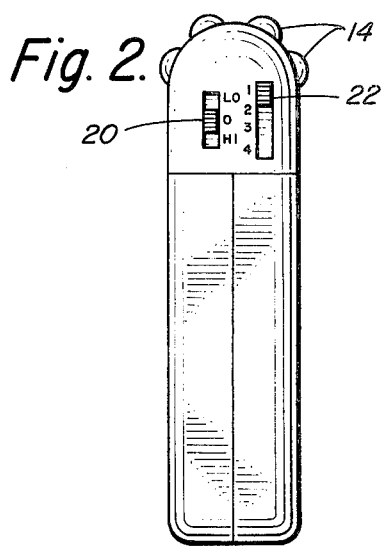
FIG. 2 is a side elevation of the electrical stimulation and massage device.
Figure 3:
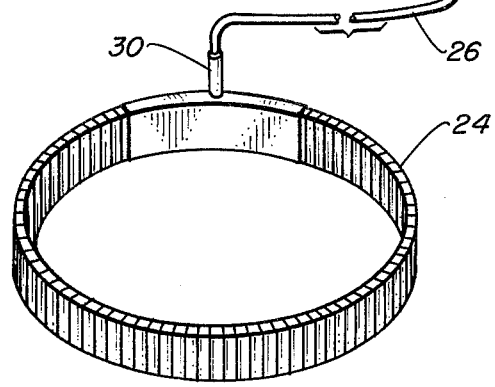
FIG. 3 is a top plan view of the electrical stimulation and massage device.

Referring to FIG. 1, there is shown an electrical stimulation and massage device enclosed in a case or housing 10 and having a roller massage head 12 for massaging while simulataneously electrically stimulating an area to be treated. The massage head 12 is formed of a plurality of elongate rollers 14 mounted at their ends on bearings (not shown) and electrically connected to a pulse-generating circuit which will be described in greater detail hereinafter. A battery to provide a power supply for the electronic circuit of the device is contained in a compartment provided with a removable cover 16. In addition to the roller electrode massage head 12, there is also provided a ball electrode 18 at one side of the housing 10. This is also electrically connected to the pulse-generating circuit. Switches 20 and 22 in the opposite side of the case 10 permit discrete selection of four different output levels at high or low currents A unique feature of this device is the convenient expansion band indifferent electrode 24 which eliminates the need for any type of adhesive or hand-held ground connection. The flexible, expansion band 24 can easily be slipped over a wrist or ankle and is electrically connected to the electrical circuit in case 10 by a flexible wire 26. The flexible wire 26 may have plug connectors 28 and 30 which removably plug into jacks in the wristband 24 and housing 10 or may be permanently connected, if desired.

Figure 4:
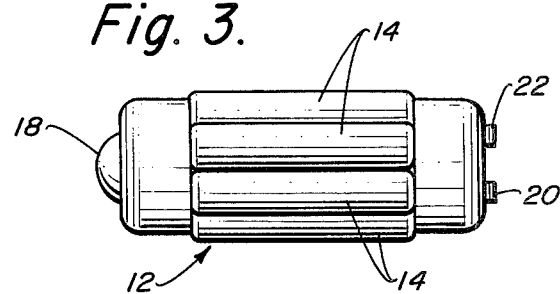
FIG. 4 is a block diagram of the electrical circuit for producing the electrical stimulation in the massage device.

The electrical stimulation circuit is illustrated in FIG. 4. This circuit is comprised of a pulse-generating circuit which is formed by a DC power supply 32, a repetition rate timer 34, which is connected to a pulse width or duty cycle timer circuit 36. The output of this duty cycle timer is fed to a buffer circuit 40, which isolates the timing oscillator and switches the output of a 10 Khz oscillator circuit 38 to a driver circuit 42, whose output is connected to the primary of transformer T1. The voltage output of the transformer secondary is rectified by a full wave bridge rectifier 44 and is passed through a filter and current limiter 46 before being connected to the electrodes. The secondary of the transformer T1 has a plurality of taps connected to switches S1 and S2 for discretely selecting high and low-level current at four different output levels. The switch S2 is a three-position switch having a high, low and center off positions. In addition, switch S1 provides four different output levels in conjunction with the high or low-level positions of switch S2. This switch combination serves as the off/on control of the device, and provides discrete selection of voltage outputs from approximately 6 to 50 volts in increments of approximately about 6 volts each. Thus, the low-level outputs are approximately 6, 12, 18 and 24 volts, while the high-level outputs are approximately 32, 38, 44 and 50 volts. Power is supplied by a 9-volt transistor battery housed in a compartment beneath battery cover 16.

The electrical stimulator and roller massage device is designed to be used in treatment of severe chronic and acute pain. It combines the two physical energies of electrical stimulation and massage. The electricity produced by the circuit of FIG. 4 is low-energy pulsed galvanic or DC current. Transcutaneous electrical stimulation (through the skin) of nerve fibers, such as produced by the electrical stimulator and massage device of this invention, has become a widely accepted method of obtaining and providing pain relief.

The electrical massage stimulator of the invention is a battery-operated pulse generator which sends minute electrical signals or impulses through the surface of the skin to the underlying nerves by way of the roller head or ball electrodes. These nerve impulses reach the spinal cord and block or reduce the pain messages arriving there via other nerve pathways and pain is relieved. This is because the sensation of pain begins only when the pain message is received by the brain, which message travels from the affected areas along the nerves which lead to the spinal cord and from there to the brain. The pain may be due to a multitude of organic or emotional disturbances and can be felt at the site of the affected area or may be felt at a region remote from the site. The electromassage device can be used with any form of massage to promote physical well being or for treatment of tired, aching muscles.

The device is used by rolling the electric massage stimulator from the periphery of the treated area toward the brain. For aching feet or tired or sore muscles, the stimulator should be rolled over the sore areas towards the head. For joint pain the stimulator should be rolled over the painful area. More or less current depending upon the intensity of the pain may be required and can be selected by operation of switches 20 and 22 to either high or low position and the lower to higher level of switch 22.

Ball electrode 18 on the side of the case 10 can be successfully used for electric stimulation of particular points, sometimes called acupuncture or trigger points. Publications illustrating some 500 to 800 acupuncture points are available. These publications can be very helpful in the identification of points for treatment with the ball electrode 18.

One such point is the fleshly area between the thumb and forefinger of the hands and can be treated much more effetively with the ball electrode 18 than the roller head 12. The acupuncture points are treated by the ball electrode 18 being rolled with gentle pressure over the particular point selected. A distinct increase in current can be felt when the particular acupuncture point is accurately located. The amount of current used during treatment depends upon the tolerance and the amount of pain being experienced by the patient.

The electromassage stimulator device can also be effective for facial massage by stimulating circulation to the skin, and the ball electrode 18 has been shown to be effective in some cases for the treatment of acne. The ball electrode is convenient for treatment of individual small blemishes or lesions.

To operate the device the flexible wire 26 is plugged into the expansion band 24 and into the plug jack (not shown) at the bottom of the case 10. The expansion electrode 24 is then placed on the wrist or ankle to provide a convenient (indifferent) ground connection. Preferably the wrist band 24 is placed on the hand you are treating yourself with, which enhances the creation of subcutaneous current transmission through the neurological system. For convenience, the expansion band indifferent electrode 24 may be readily attached to a foot or ankle in treating lower body parts, such as the legs and thighs.

The switches 20 and 22 provide discrete selection of current amplitude. With switch 20 in the on (low or high) position, a light-emitting diode 50 connected to the buffer stage of the pulse circuit will indicate the unit is in good working order by flashing. If the light-emitting diode 50 is not flashing, then it indicates that the unit needs a battery replacement. The second switch 22 provides four different discrete output current levels for the high and low output selections. For maximum safety the output levels cannot exceed about 50 volts and may be as low as 6 volts, as described above. During treatment, the switch 20 would be in the low position with switch 22 in position 1 and the output of switch 22 increased gradually to a level which provides the necessary relief and feels comfortable. In the event that relief is not obtained on the low output setting of switch 20, it should be advanced to the high output position with switch 22 in position 1, and the output of switch 22 increased until relief is obtained. The sensation and tolerance for the electrical stimulation differs from person to person and some patients need and can tolerate more output and higher current levels than others.

Thus, there has been described an electromassage stimulating device which provides treatment over large areas with a roller electrode head and treatment of particular acupuncture points with a ball electrode. The construction and arrangement of the ground electrode permits ease and convenience of use with no adhesives or special connections needed for use of the device.

Obviously, many modifications and variations of the present invention are possible in light of the above teachings. It is therefore to be understood that the full scope of the invention is not limited to the details disclosed herein and may be practiced otherwise than as specifically described.

What is claimed is:

1. An electrical stimulator and massage apparatus comprising:
   a housing;

a plurality of elongate, adjacent roller electrodes forming a massaging head in said housing;

electrical means for applying an electrical pulse to said roller electrodes;

a flexible expansion band indifferent electrode which may be slipped over a wrist or ankle whereby a particular area of the body may be mechanically massaged and electroneurologically stimulated simultaneously; and means for connecting said expansion band electrode to said electrical means.

2. The apparatus according to claim 1 including:

a separate point electrode mounted in said housing.

3. The apparatus according to claim 2 wherein said separate point electrode comprises:

a roller ball for massaging particular neurological treatment points.

4. The apparatus according to claim 1 wherein said electrical means comprises:

a pulse-generating circuit having a predetermined frequency and width;

a transformer for connecting the output of said pulse generator to said roller electrodes; and means for discretely varying the amplitude of the output from said transformer.

5. The apparatus according to claim 4 wherein said means for varying the output amplitude comprises:

discrete means for selecting various output positions on the secondary of said transformer.

6. The apparatus according to claim 5 wherein said discrete means comprises:

a first switch for selecting a high or low tap position on the secondary of said transformer, said switch including an off position;

a second switch for selecting one of a plurality of taps on the secondary of said transformer; and whereby discretely varied output amplitudes with said first switch in the high or low position may be selected.

7. The apparatus according to claim 1 including indicating means indicating the operation of said pulse-generating circuit.

8. The apparatus according to claim 7 wherein said indicating means comprises a light-emitting diode operated by said pulse-generating circuit.

* * * * *